US00PP19798P2

(12) United States Plant Patent

Van Spronsen

(10) Patent No.: US PP19,798 P2

(45) Date of Patent: Mar. 3, 2009

(54) *CHRYSANTHEMUM* PLANT NAMED 'POWER WHITE'

(50) Latin Name: *Chrysanthemum ×morifolium*
Varietal Denomination: Power White

(75) Inventor: Simon Van Spronsen, Niagara on the Lake (CA)

(73) Assignee: Willy's Greenhouse Ltd., Niagara on the Lake (CA)

( * ) Notice: Subject to any disclaimer, the term of this patent is extended or adjusted under 35 U.S.C. 154(b) by 0 days.

(21) Appl. No.: 12/011,823

(22) Filed: Jan. 30, 2008

(51) Int. Cl.
*A01H 5/00* (2006.01)

(52) U.S. Cl. ..... Plt./294

(58) Field of Classification Search ..... Plt./294
See application file for complete search history.

*Primary Examiner*—Annette H Para
(74) *Attorney, Agent, or Firm*—Penny J. Aguirre

(57) ABSTRACT

A new cultivar of *Chrysanthemum,* 'Power White', characterized by it's early and free flowering habit, its daisy-type inflorescences with bright white ray florets and bright yellow disk florets, its vigorous freely branched growth habit, its dark green foliage and its uniform, rounded and outward spreading plant habit.

2 Drawing Sheets

Botanical classification: *Chrysanthemum×morifolium.*
Variety denomination: 'Power White'.

BACKGROUND OF THE INVENTION

The present invention relates to a new and distinct cultivar of *chrysanthemum* plant, botanically known as *Chrysanthemum×morifolium* 'Power White' and hereinafter by its cultivar name, 'Power White'.

The new *chrysanthemum* 'Power White' was discovered by the inventor as a naturally occurring branch mutation of the *Chrysanthemum* cultivar 'White Cherie' (U.S. Plant Pat. No. 9,845) in July 2007 in Niagara on the Lake, Ontario, Canada.

Asexual reproduction of the new cultivar was first accomplished via stem cuttings in July 2007 in Niagara on the Lake, Ontario, Canada. The characteristics of this cultivar have been determined to be stable and are reproduced true to type in successive generations.

SUMMARY OF THE INVENTION

The following traits have been repeatedly observed and are determined to be the characteristics of the new cultivar of *Chrysanthemum.* These attributes in combination distinguish by 'Power White' as unique from all other varieties of *Chrysanthemums* known to the inventor.

1. 'Power White' is early flowering with daisy-type inflorescences about 3.8 cm in diameter.
2. The inflorescences of 'Power White' have bright white ray florets with bright yellow disk florets.
3. 'Power White' has a freely branched, uniform, rounded and outward plant habit.
4. 'Power White' has a uniform flowering response.
5. 'Power White' has dark green foliage.
6. 'Power White' is a vigorous grower.

In comparison to the parent plant, 'White Cherie', 'Power White' has brighter white colored ray florets and bright yellow disk florets whereas 'White Cherie' has creamy white ray florets and disk florets that are more golden in color.

Based on its growth habit, flowering response and flower type, 'Power White' can be most closely compared to 'Apricot Cherie' (U.S. Plant Pat. No. 12,691) which has soft pink to tan colored ray florets and 'Power Yellow' (U.S. Plant Pat. No. 18,175) which has yellow ray florets.

BRIEF DESCRIPTION OF THE DRAWINGS

The accompanying colored photographs illustrate the overall appearance and distinct characteristics of the new *Chrysanthemum.* 'Power White'. The photographs were taken of a plant grown in a 5-inch pan pot planted with 3 rooted cuttings and grown under greenhouse conditions for 10 weeks.

Figure 1:
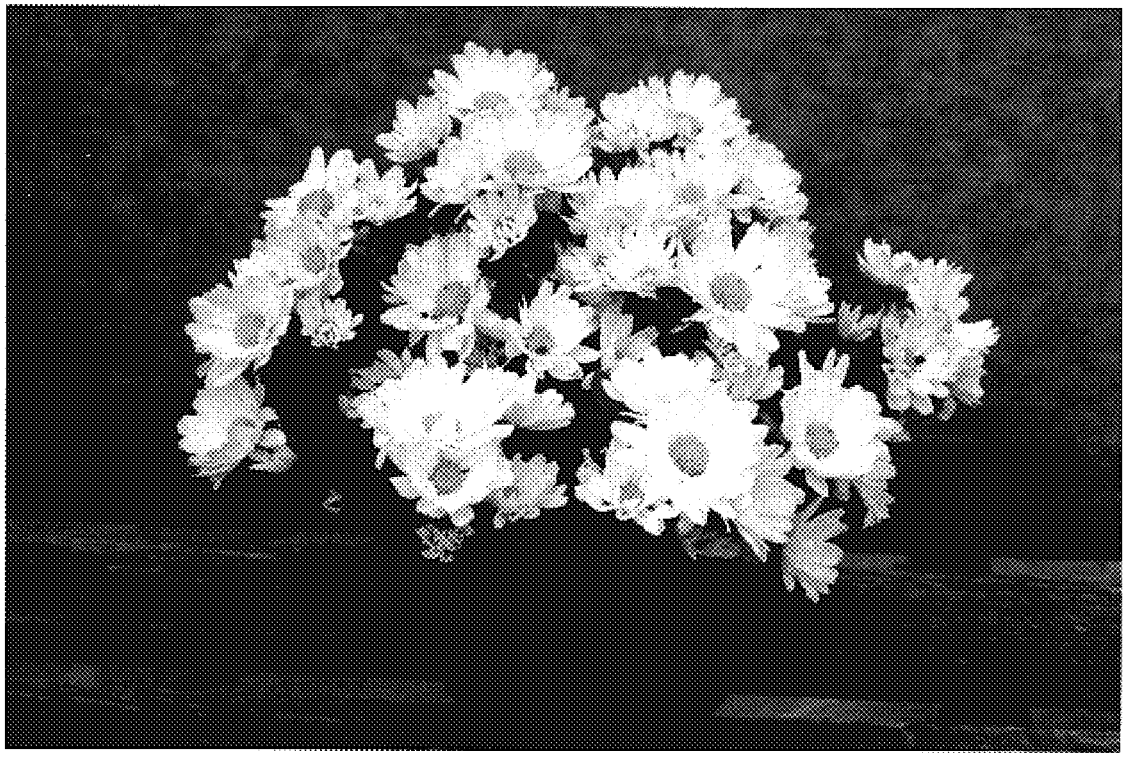
FIG. 1 is a photograph that provides a side perspective view of a typical plant in bloom when grown as a spray-type.
Figure 2:
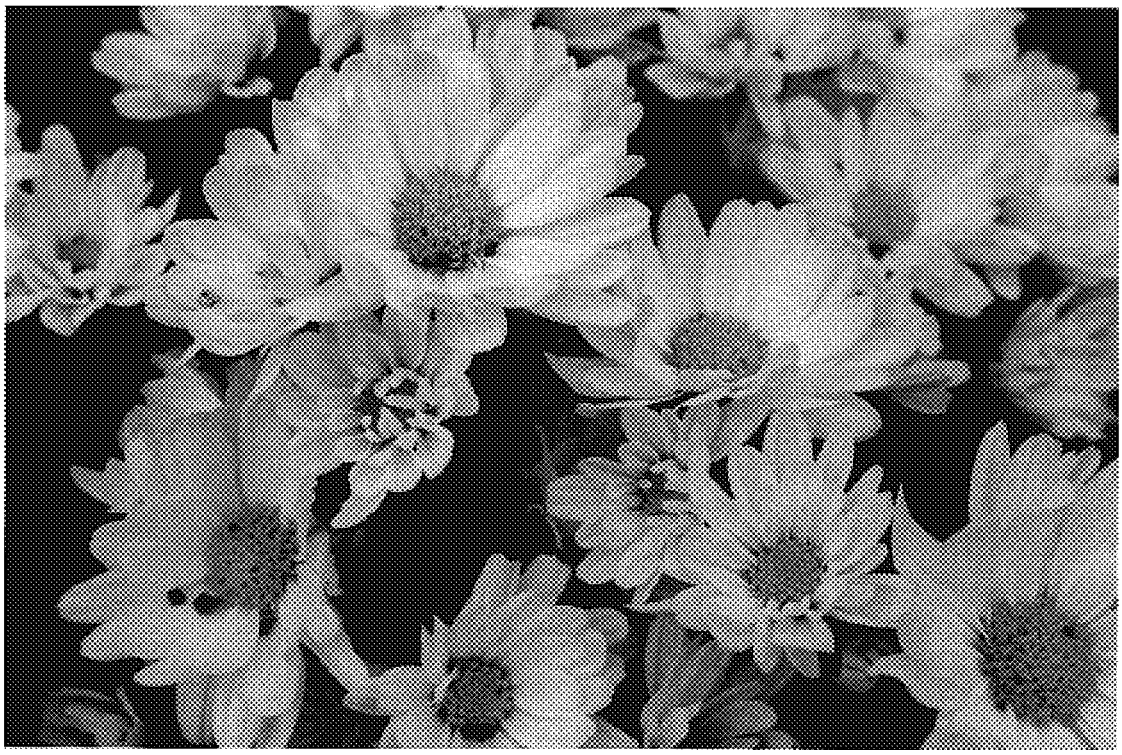

The photograph in FIG. 2 provides a close-up view of the inflorescences of 'Power White'.

The colors in the photographs are as close as possible with the photographic and printing technology utilized. The color values cited in the detailed botanical description accurately describe the colors of the new *Chrysanthemum.*

DETAILED BOTANICAL DESCRIPTION

The following is a detailed description of plants of the new cultivar as grown in a 5-inch pan pot planted with 3 single pinched rooted cuttings and grown under greenhouse conditions at an average temperature of 65° F. for 10 weeks. The phenotype of the new cultivar may vary with variations in environmental, climatic, and cultural conditions, as it has not been tested under all possible environmental conditions. The color determination is in accordance with the 2001 R.H.S. Colour Chart of The Royal Horticultural Society, London, England, except where general color terms of ordinary dictionary significance are used.

General description:

*Commercial classification.*—Daisy-type potted *Chrysanthemum.*

*Flowering response.*—Flowering occurs after short day treatment in about 52 days in spring, summer and fall and 56 days in winter.

*Plant type.*—Herbaceous, grown as a potted *Chrysanthemum* as a spray-type.

*Plant habit.*—Freely branched, uniform, outward plant habit with rounded crown.

*Height and spread.*—Reaches about 15 cm in height and 26 cm in width when grown under the conditions tested under greenhouse conditions.

*Diseases resistance.*—No susceptibility or resistance to diseases common to *Chrysanthemum* has been observed under commercial greenhouse productions.

*Root description.*—Fibrous.

Growth and propagation:

*Propagation.*—Terminal stem cuttings.

*Time to root.*—About 8 days at 20° C.

*Production.*—Rooted cuttings grown on at 65° F. finish in a 5-inch pan pot in 8 weeks.

*Growth rate.*—Vigorous.

Stem description:

*Stem color.*—144A with pubescence of 144D.

*Stem strength.*—Strong and flexible.

*Stem surface.*—Pubescent.

*Branching habit and quantity.*—Freely branched, about 5 branches per stem after removal of the apical meristem (pinching).

*Lateral branch size.*—About 8 cm in length and about 3 mm in width.

*Internode length.*—Lateral branches primarily in a whorl from pinched node, secondary flowering stems about 1 cm.

Foliage description:

*Leaf division.*—Simple.

*Leaf shape.*—Blade is broadly ovate with narrowing towards base.

*Leaf base.*—Blade base is cuneate, leaf base truncate.

*Leaf apex.*—Rounded to acute and mucronate.

*Leaf margin.*—Matures to trifid with mucrunate tips on lobes.

*Leaf texture.*—Upper surface slightly pubescent, lower surface pubescent.

*Leaf venation.*—Palmate, upper surface 137B, lower surface 138B.

*Leaf attachment.*—Sessile.

*Leaf arrangement.*—Alternate.

*Leaf number.*—Average of 10 per lateral branch.

*Leaf internode length.*—Average of 9 mm.

*Leaf color.*—Young foliage; upper surface 139A, lower surface 189A, mature foliage; upper surface 137A, lower surface a color between 191A and 191B.

*Leaf size* (*fully expanded*).—Average of 4.5 cm in length and 2.4 cm in width (expanded blade portion is an average of 3 cm).

*Fragrance of foliage.*—Fragrant if bruised.

Flower description:

General description:

*Inflorescence type.*—Composite, daisy form with oblong shaped ray florets and disk flowers arranged acropetally on a capitulum, inflorescences typically borne in compound corymbs.

*Postproduction longevity.*—Conditions dependent, inflorescences maintain good color and substance for about 2 weeks in an interior environment.

*Fragrance.*—Faint.

*Quantity of inflorescences.*—Average of 11 per lateral stem, about 170 per plant produced from 3 cuttings.

*Inflorescence buds.*—About 8 mm in depth and 7 mm in diameter, globose in shape, 155A in color with phyllaries 138A to 138B.

*Inflorescence size.*—About 1 cm in depth and 3.8 cm in diameter, diameter of disk about 9 mm.

*Peduncle.*—Strong, flexible, held from upright to an angle of 30° to vertical, surface is pubescent, an average of 2.2 cm in length and 2 mm in width, 138B in color.

*Involucral bracts* (*phyllaries*).—Arranged in two layers, 138A in color with translucent margins, about 4 mm in length and 1.2 mm in width, surface is pubescent.

*Receptacle.*—About 3 mm in diameter, 137B in color.

Ray florets (capitulate):

*Number.*—Average of 28.

*Arrangement.*—In 3 rows.

*Shape.*—Elongated oblong.

*Aspect.*—Ranges from horizontal to a 45° angle when fully open.

*Size.*—Average of 1.8 cm in length and 6 mm in width.

*Petal apex.*—Rounded with tip mucronulate or notched.

*Petal base.*—Cuneate.

*Petal margins.*—Entire.

*Petal texture.*—Glabrous on upper and lower surface and ridged.

*Petal color.*—Opening and fully open, upper and lower surface; whiter than 155B, base surrounding pistil N144A.

Disk florets (perfect):

*Arrangement.*—Massed in center of receptacle.

*Quantity.*—Average of 65.

*Shape.*—Tubular.

*Size.*—About 4 mm in length and about 1 mm in width.

*Color.*—Immature 1A to 1B, mature 7A.

Reproductive organs:

*Presence.*—Disk flowers are perfect, ray flowers are carpellate.

*Gynoecium.*—1 Pistil per disk and ray floret, 3.5 mm in length, style color 1C, stigma color 7C.

*Androcoecium.*—5 stamens per disk floret, fused into tube surrounding style, anthers are translucent and color 13C, pollen is moderate in quantity and 17A in color.

*Seed.*—Seed production has not been observed under the conditions tested.

It is claimed:

1. A new and distinct cultivar of *Chrysanthemum* plant named 'Power White' as herein illustrated and described.

* * * * *